United States Patent [19]
Aida et al.

[11] Patent Number: 4,759,747
[45] Date of Patent: Jul. 26, 1988

[54] BREAST PUMP INCLUDING PRESSURE ADJUSTING MEANS

[75] Inventors: Shigeru Aida; Hiroyuki Uehara, both of Tokyo, Japan

[73] Assignee: Pigeon Company, Ltd., Tokyo, Japan

[21] Appl. No.: 921,252

[22] Filed: Oct. 21, 1986

[30] Foreign Application Priority Data

Oct. 21, 1985 [JP] Japan .................................. 60-233309

[51] Int. Cl.$^4$ ................................................. A61M 1/06
[52] U.S. Cl. ..................................................... 604/74
[58] Field of Search ................... 119/14.44; 604/74–76, 604/315; 137/82, 540 C

[56] References Cited

U.S. PATENT DOCUMENTS 2,169,992  8/1939  Shurts ................................. 119/14.44
4,673,388  6/1987  Schlensog ................................ 604/74

FOREIGN PATENT DOCUMENTS 2087646  8/1978  Fed. Rep. of Germany ........ 604/75
2127293  4/1984  United Kingdom .................. 604/74

Primary Examiner—C. Fred Rosenbaum
Assistant Examiner—J. L. Kruter
Attorney, Agent, or Firm—Wenderoth, Lind & Ponack

[57] ABSTRACT

A milking apparatus for extracting milk from a human breast has a funnel shaped receiver positionable over the breast attached to a conduit and receiver bottle for receiving extracted milk. An adaptor is provided such that different types of suction pumps may be used in conjunction with the apparatus in response to the needs of the user. A pressure adjusting mechanism is associated with the adaptor which is operated automatically or manually to relieve excess suction exerted by a selected suction pump on the breast.

2 Claims, 3 Drawing Sheets

BREAST PUMP INCLUDING PRESSURE ADJUSTING MEANS

BACKGROUND OF THE INVENTION

1. Field of the Invention

The present invention relates to a milking apparatus, i.e. a breast pump, for extracting milk from the breast of a woman.

2. Description of the Prior Art

Conventional milking apparatuses generally comprise a funnel shaped receiver positionable over a breast and attached at one end to a conduit. The other end of the conduit is attached to a collecting bottle. A suitable suction means is employed to create suction in the funnel shaped receiver to extract milk from the breast which is deposited in the collecting bottle through the conduit.

Known suction means include a diaphragm type electric suction pump and a bulb type hand suction pump having a spherical rubber grasp, the gripping type pump being capable of producing a greater suction than the diaphragm type pump.

Such conventional milking apparatuses comprise either the diaphragm type pump or the bulb type pump.

Thus, under some circumstances, such as the birth of a second child when the first child is still quite young, a milking apparatus providing a small amount of suction may be used such as one employing the diaphragm type pump. However, after the passage of an appreciable amount of time an apparatus providing a greater suction may be required to sufficiently extract milk and a milking apparatus employing the bulb type pump must be used.

Therefore, it may often be necessary for the same user to use two completely different sets of milking apparatuses, each comprising a funnel shaped receiver, conduit, receiving bottle and respective suction pump when circumstances and the needs of the user change in regard to the suction requirements of the apparatus.

SUMMARY OF THE INVENTION

An objective of the present invention is to overcome the above-mentioned need for two completely different sets of milking apparatuses. The present invention provides an adaptor to which either a diaphragm type pump or a bulb type pump may be detachably mounted.

Another object of the invention is to provide a pressure adjusting means that may relieve the suction exerted by either of the detachably mounted pumps when that pressure exceeds a predetermined maximum. A further provision of the pressure adjusting means is that the predetermined maximum pressure may be set and varied by a separate adjustment of the pressure adjusting means.

These and other objects of the present invention will become more fully apparent to those of ordinary skill in the art from the following description and appended claims taken in conjunction with the accompanying drawings.

DETAILED DESCRIPTION OF THE PREFERRED EMBODIMENT

Figure 1:
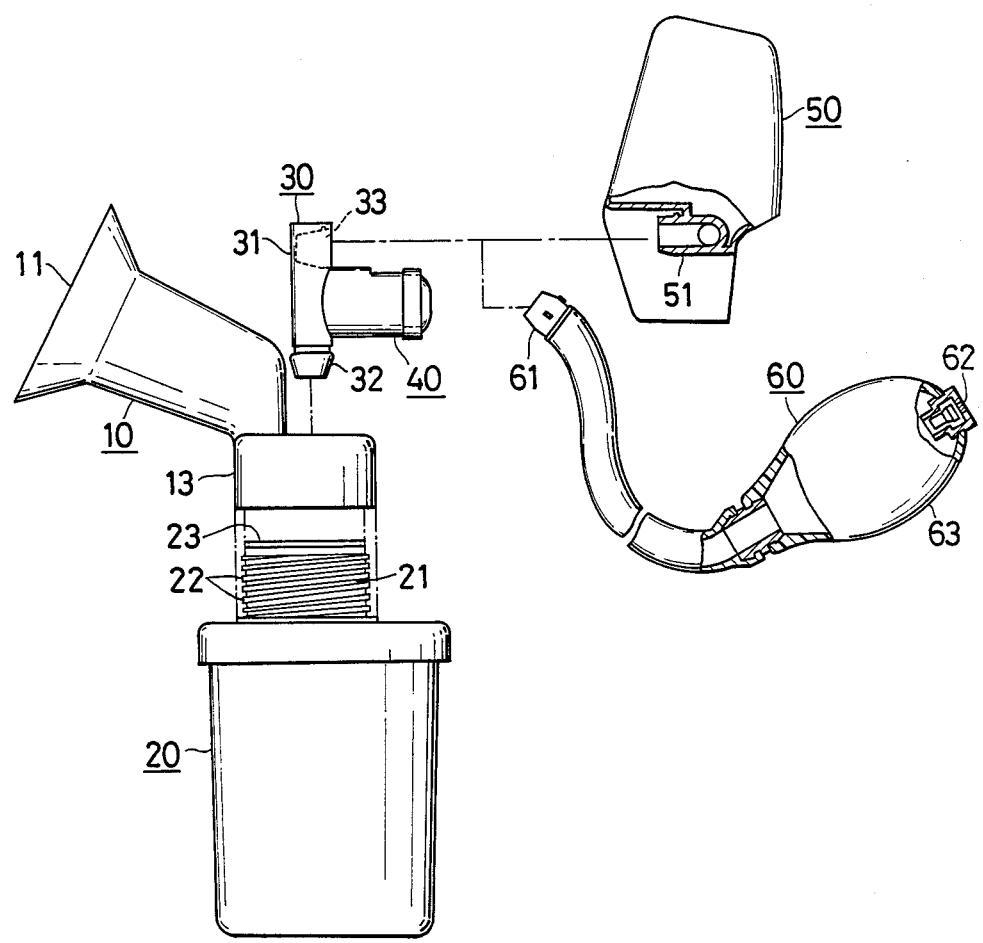
FIG. 1 is an exploded front view of an embodiment of the milking apparatus according to the present invention.
Figure 2:
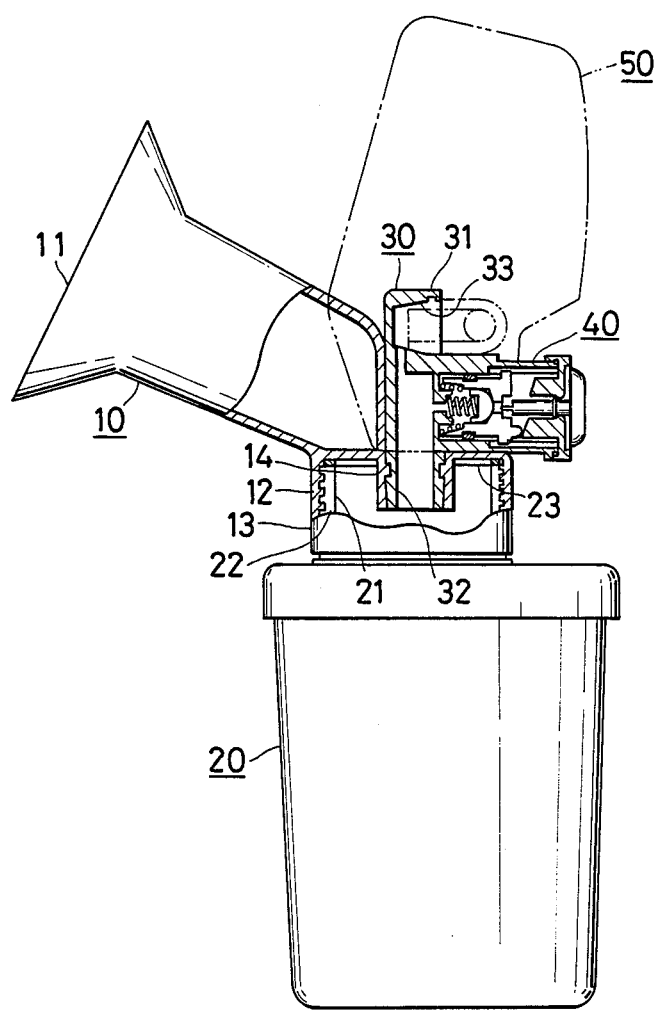
FIG. 2 is a front view partly cut away of the present invention.

In FIGS. 1 and 2 a funnel shaped receiver 11 is formed on the end of a conduit 10. On the other end of the conduit 10 is a coupling 13 having a mounting means 12 for mounting the coupling 13, conduit 10 and receiver 11 to an upstanding neck 21 of a bottle 20.

In the preferred embodiment the mounting means 12 comprises an internal screw thread which mates with an external screw thread 22 formed on the upstanding neck 21. A packing 23 may be inserted between the upstanding neck and the coupling as shown in FIG. 2. When the bottle 20 is removed from the coupling, a conventional nipple is capable of being mounted to the neck 21.

An adaptor 30 is detachably mounted to the coupling 13 of the conduit 10 as also shown in FIG. 2. The adaptor 30 comprises tubular connecting member 31. A connecting portion 32 formed at one end of the connecting member 31 is adapted to engage a connecting portion 14 of the coupling 13 thereby securing the adaptor 30 to the coupling. A connecting recess 33 is provided in the other end of the tubular connecting means 31.

The connecting recess 33 may be engaged by a connection member 51 of a diaphragm type pump 50 or by a connection member 61 of a bulb type hand pump 60.

The inner structure of the diaphragm type electric suction pump 50 is conventional and comprises a reciprocated diaphragm, and inlet and exhaust valves to create a differential pressure between the atmosphere and an inner suction space. This pressure difference (suction) is subjected to the breast via the adaptor 30, coupling 13 and conduit 10 open to the coupling and receiver 11.

Likewise, the bulb type hand suction pump 60 may be used. A squeeze bulb 63 having an exhaust valve 62 can be squeezed to produce suction.

Also provided on the adaptor 30 is a pressure adjusting means 40. The pressure adjusting means 40 serves essentially three functions. First, it automatically relieves the suction exerted on the breast by either of the suction pumps 50, 60 when that suction exceeds a predetermined maximum, the maximum being below an amount that would cause pain or discomfort. Second, the pressure adjusting means provides for adjustability of the predetermined maximum. And third, the pressure adjusting means may be manually actuated to quickly relieve the suction in, for example, an emergency situation.

Figure 3:
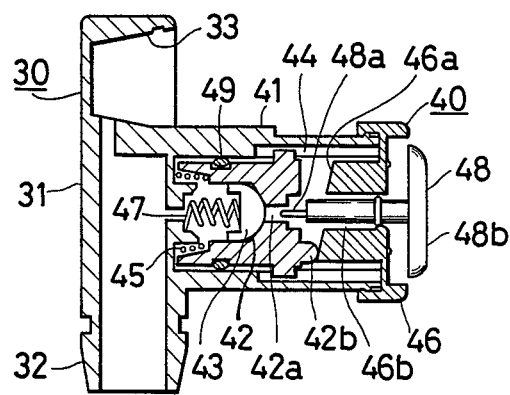
FIG. 3 is a cross sectional view of the apparatus for adjusting pressure in the present invention.

As illustrated in FIG. 3 the pressure adjusting means 40 comprises a valve seat 42 slidably mounted in a hollow tube 41 along splines 44 of the tube. The valve seat is fixed in place between a cam member 46 having an inclined face 46a contacting a projection 42b of the valve seat and a spring 45. An O-ring 49 forms a seal between the valve seat 42 and the inner periphery of the tube 44.

A valve 43 is loosely received within the valve seat 42. A spring 47 urges the valve 43 against a first air inflow hole 42a extending through the valve seat and communicating with the atmosphere. An auxilliary hole provided in the tubular connecting means 31 is open to and communicates with the space in which the valve 43 is received within the valve seat 42. This auxilliary hole only communicates with the air inflow hole 42a when the valve 43 is urged away from the valve seat 42 and air inflow hole 42a due to the loose fit of the valve 43 within the valve seat 42.

Another air inflow hole 46b extends through the cam member 46 and is open to the air inflow hole 42a and the atmosphere. A release member 48 for instantly pressing the valve 43 out of contact with the valve seat 42 is provided loosely in the air inflow hole 46b of the cam member 48 such that air from the atmosphere may enter the hole 46b. The release member 48 has a pointed pin 48 which will contact the valve 43 through the air inflow hole 42a to urge the valve 43 off of the valve seat 42 when the release member is pushed.

In operation, the suction pumps 50 or 60 create suction which is applied to the breast through an air passageway in the tubular connecting means of the adaptor 30 and receiver 11 as mentioned above.

When this suction increases beyond a predetermined maximum valve, e.g. one that is just about to cause pain or discomfort, the valve seat 43 also subject to the suction through the above-mentioned auxilliary hole formed in the tubular means 31, is urged by the suction and atmospheric pressure acting on the valve through air inflow hole 42a off of the valve seat 42 and air inflow hole 42a against the force exerted by spring 47. Accordingly, air from the atmosphere enters the adaptor 30 through the hole formed in the tubular means 31 and air inflow holes 42a and 46b due to the differential pressure between the vacuum created in the adaptor by the suction pump and atmospheric pressure. Thus, the addition of air at atmospheric pressure counteracts the suction generated by the suction pump, and the suction on the breast is reduced. Once an equilibrium is established the spring will then urge the valve 43 back against the valve seat 42 and the air inflow hole 42a whereby the above-mentioned operation is repeated. Because such an intermittent motion is imparted to the valve 43, the resulting fluctuation in suction exerted on the breast will have a stimulating effect to accelerate the secretion of milk.

The static position of the valve seat 43 may be adjusted such that different predetermined maximum amounts of suction will be required to move the valve 43 off of the valve seat 42 and air inflow hole 42a. This is accomplished by rotating the cam member 40 mounted to the tube 41. Thus the inclined cam surface 46a is rotated over the projection 42b of the valve seat 42 whereby the valve seat is guided by splines 44 along the inside of the tube 41 by or against the force exerted by a spring 45. Therefore, spring 47 is adjusted to expand or contract with the movement of the valve seat 42 as urged by the valve 43 contacting the valve seat. Thus the initial displacement of the springs 47 is adjustable and accordingly the force (predetermined maximum suction) required to urge the valve 43 off of the valve seat 42 against the force of the spring 47 is made variable since the spring force to be counteracted by the predetermined maximum suction is dependent on the initial displacement of the spring.

Finally, when unexpected pain has been felt or the milking operation is finished the release member 48 may be pressed to instantaneously move the valve 43 off of the valve seat 42 to communicate the adaptor 30 with the atmosphere and reduce the suction on the breast.

Other advantages of the present invention include that the adaptor 30 and suction pump 50 or 60 may be removed and the most soiled parts 10, 11, 12 and 20 may be washed frequently. This capability reduces the need for washing the adaptor including the adjustment means and/or the pump which would shorten the life thereof.

Also only damaged parts need to be replaced since the apparatus can be easily taken apart and reconstructed.

Obviously many modifications and variations of the present invention are possible in light of the foregoing description. It is therefore to be understood that within the scope of the appended claims, the invention may be practiced otherwise than as specifically described.

What is claimed is:

1. A milking apparatus for extracting milk, comprising:

a receiver having an open end for receiving the extracted milk;

a conduit extending from the other end of the receiver and through which milk received by said receiver passes, said conduit comprising a coupling member adapted for coupling a milk collection bottle to said conduit; and an adaptor detachably connected to said coupling member of said conduit, said adaptor comprising securing means for securing a suction pump to said adaptor, a tubular means extending from said securing means and having an air passageway extending therethrough open to and communicating with said securing means and said conduit for allowing suction generated by a suction pump secured to said securing means to act therethrough and through said conduit and said receiver such that milk is extracted from a breast over which said receiver is positioned when suction is generated by the secured suction pump, said tubular means having an auxiliary hole open to and communicating with said air passageway, and a pressure adjusting means attached to said tubular means over said auxiliary hole for communicating with said air passageway via said auxiliary hole for reducing suction acting through said air passageway to reduce the suction acting through the tubular means, said pressure adjusting means comprising a tube having one end disposed around said auxiliary hole and another end open to and communicating with the atmosphere, a valve seat slidably mounted within said tube and having a first cylindrical end located around said auxiliary hole and open thereto and a second end having a first air inflow hole open to and communicating with said another end of said tube open to and communicating with atmosphere, a valve loosely received within said first cylindrical end of said valve seat and a spring extending within said first cylindrical end of said valve seat and connected to said tubular means around said auxiliary hole and to said valve for urging said valve against said valve seat to cover said first air inflow hole for preventing air from the atmosphere from entering therethrough past said loosely received valve to said air passageway via said auxiliary hole when the suction acting through said air passageway of said tubular means is below a predetermined maximum, and means for adjusting the position of the slidable valve seat within said tube such that the displacement of said spring urging said valve against said valve seat is adjusted with the adjustment of said valve seat and the value of said predetermined maximum is accordingly changed, said means for adjusting the position of said valve seat within said tube comprising a spring means within said tube connected between said tubular means and said first cylindrical end of said valve seat and a cam member rotatably secured to said other end of said tube and having an inclined cam face extending within said tube abutting said second end of said valve seat at a portion thereof spaced from said first air inflow hole for being rotated about said tube for causing said inclined cam face to move over said portion of said second end of said valve seat to slide said valve seat to position said valve seat within said tube.

2. An appratus as claimed in claim 1 wherein, said cam member has a second air inflow hole extending therethrough open to and communicating with said first air inflow hole and the atmosphere; and further comprising a release member loosely secured within said second air inflow hole, said release member having a first pin-like end disposed within said tube coaxial with said first air inflow hole and a second end exterior of said tube and said cam member for being manually pressed to push said pin-like end to move through said first air inflow hole and urge said valve urged by said spring against said second end of said valve seat and said first air inflow hole off of said valve seat and said first air inflow hole for rapidly communicating said air passageway with the atmosphere for rapidly reducing the suction acting through said air passageway of said tubular means.

* * * * *